United States Patent [19]

Seele et al.

[11] Patent Number: 5,128,357
[45] Date of Patent: Jul. 7, 1992

[54] 1-ALKOXY-1-AZOLYLMETHYLOXYIRANES AND THE USE THEREOF AS CROP PROTECTION AGENTS

[75] Inventors: Rainer Seele; Reiner Kober, both of Fussgoenheim; Norbert Goetz, Worms; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 747,510

[22] Filed: Aug. 20, 1991

Related U.S. Application Data

[63] Continuation of Ser. No. 492,806, Mar. 13, 1990, abandoned.

[51] Int. Cl.$^5$ .............. A01N 43/653; C07D 249/08
[52] U.S. Cl. ................................. 514/383; 514/184; 548/101; 548/268.2
[58] Field of Search .............. 548/101, 268.2; 514/184, 383

[30] Foreign Application Priority Data

Apr. 6, 1989 [DE] Fed. Reg. of Germany .......... 3911059

[56] References Cited

FOREIGN PATENT DOCUMENTS 3218130 11/1983 European Pat. Off. .

OTHER PUBLICATIONS

Ogata et al., "Preparation of bis (azolyl) etc." CA 108: 112463h (1988).
Ogata et al., "Synthesis and oral antifungal" CA 111: 194666a (1989).
RN 112669—40-6.
RN 123365—27-5.

*Primary Examiner*—Patricia L. Morris
*Attorney, Agent, or Firm*—Oblon, Spivak, McClelland, Maier & Neustadt

[57] ABSTRACT

1-Alkoxy-1-azolylmethyloxiranes of the general

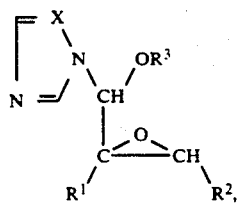

where $R^1$ and $R^2$ are identical or different and each is $C_1-C_8$-alkyl, $C_3-C_8$-cycloalkyl, $C_5-C_8$-cycloalkenyl, tetrahydropyranyl, norbornyl, pyridyl, naphthyl, biphenylyl or phenyl, each of which is unsubstituted or mono- to trisubstituted by halogen, nitro, phenoxy, amino, alkyl, alkoxy or haloalkyl of 1 to 4 carbon atoms in each case, $R^3$ is $C_1-C_4$-alkyl, X is CH or N, the acid addition salts and metal complexes thereof which are tolerated by plants, processes for their manufacture, and their use for combating fungi.

6 Claims, No Drawings

1-ALKOXY-1-AZOLYLMETHYLOXIRANES AND THE USE THEREOF AS CROP PROTECTION AGENTS

This application is a continuation of application Ser. No. 07/492,806, filed on Mar. 13, 1990, now abandoned.

The present invention relates to novel azole compounds, the preparation thereof and fungicides containing these, and methods for combating fungi.

The use of cis-2-(1,2,4-triazol-1-ylmethyl)-2-tert-butyl-3-(4-chlorophenyl)oxirane as a fungicide has been disclosed (DE-A 3218130). However, the fungicidal action is unsatisfactory in some cases.

We have now found that 1-alkoxy-1-azolylmethyloxiranes of the formula I

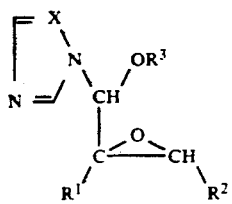

where $R^1$ and $R^2$ are identical or different and each is $C_1$-$C_8$-alkyl, $C_3$-$C_8$-cycloalkyl, $C_5$-$C_8$-cycloalkenyl, tetrahydropyranyl, norbornyl, pyridyl, naphthyl, biphenylyl or phenyl, each of which can be substituted once to three times by halogen, nitro, phenoxy, amino, alkyl, alkoxy or haloalkyl of 1 to 4 carbons in each case, $R^3$ is $C_1$-$C_4$-alkyl, X is CH or N, and the acid addition salts and metal complexes thereof which are tolerated by plants, have a better fungicidal action than known azole compounds.

The compounds of the formula I contain asymmetric carbons and can therefore exist as enantiomers and diastereomers. Mixtures of diastereomers of the compounds according to the invention can be separated in a conventional manner, for example on the basis of their different solubilities or by column chromatography, and the pure diastereomers can be isolated. Racemates of the compounds according to the invention can be resolved by conventional methods, for example by formation of a salt with an optically active acid, separation of the diastereomeric salts and liberation of the enantiomers with a base. It is possible to use both the pure diastereomers or enantiomers and the mixtures thereof produced in the synthesis as fungicidal agents.

Examples of $R^1$ and $R^2$ are $C_1$-$C_4$-alkyl, methyl, ethyl, isopropyl, n-propyl, n-butyl, sec-butyl, tert-butyl, n-pentyl, neopentyl, 1-naphthyl, 2-naphthyl, p-biphenylyl, phenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 3-chloro-6-fluorophenyl, 2-methoxyphenyl, 3-methoxyphenyl, 4-methoxyphenyl, 2,4-dimethoxyphenyl, 4-ethylphenyl, 4-isopropylphenyl, 4-tert-butylphenyl, 4-tert-butyloxyphenyl, 2-chloro-4-fluorophenyl, 2-chloro-6-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-aminophenyl, 2-trifluoromethylphenyl, 3-trifluoromethylphenyl, 4-trifluoromethylphenyl, 4-phenylsulfonylphenyl, 3-pyridyl, tetrahydropyranyl, cyclopropyl, cyclopentyl, cyclohexyl, 2-cyclohexenyl, 3-cyclohexenyl and norbornyl.

Examples of acid addition salts are the hydrochlorides, bromides, sulfates, nitrates, phosphates, oxalates or dodecylbenzenesulfonates. The activity of the salt derives from the cation so that the nature of the anion is generally immaterial. The salts of the active ingredient according to the invention are prepared by reacting the 1-alkoxy-1-azolylmethyloxiranes I with suitable acids.

Metal complexes of the active ingredients I or salts thereof can be formed with metals such as copper, zinc, tin, manganese, iron, cobalt or nickel, by reacting the 1-alkoxy-1-azolylmethyloxiranes with corresponding salts, e.g. the chlorides or sulfates such as zinc chloride, copper sulfate, tin chloride, manganese sulfate or iron sulfate.

The compounds of the formula I can be prepared by, for example, reacting a compound of the formula II

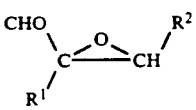

where $R^1$ and $R^2$ have the stated meanings, with a compound of the formula III

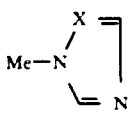

where Me is hydrogen or a metal (e.g. Na or K) and X has the stated meaning, in the presence of a thionyl halide and of an alcohol of the formula IV $$R^3OH \qquad \text{IV}$$

where $R^3$ has the abovementioned meaning.

The reaction is carried out in the presence or absence of a solvent or diluent, generally at from $-30°$ to $80°$ C. The preferred solvents and diluents include nitriles such as acetonitrile or propionitrile, ethers such as tetrahydrofuran, diethyl ether, dimethoxyethane, dioxane or isopropyl ether and, in particular, hydrocarbons and chlorohydrocarbons such as pentane, hexane, toluene, methylene chloride, chloroform, carbon tetrachloride, dichloroethane or mixtures thereof.

The novel starting compounds II are obtained, for example, by epoxidation of the corresponding olefins V

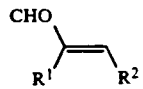

where $R^1$ and $R^2$ have the abovementioned meanings, with peroxycarboxylic acids such as perbenzoic acid, 3-chloroperbenzoic acid, 4-nitroperbenzoic acid, monoperphthalic acid, peracetic acid, perpropionic acid, permaleic acid, monopersuccinic acid, perpelargonic acid or trifluoroperacetic acid in inert solvents, preferably chlorinated hydrocarbons, e.g. methylene chloride, chloroform, carbon tetrachloride or dichloroethane, or in organic acids such as acetic acid, in esters such as ethyl acetate, in ketones such as acetone or in amides such as dimethylformamide, in the presence or absence of a buffer such as sodium acetate, sodium carbonate, disodium hydrogen phosphate or ethylenediaminetetraacetic acid. The reaction is generally carried out at from 10° to 100° C. and can be catalyzed with, for example, iodine, sodium tungstate or light. Also suitable for the oxidation are alkaline solutions of hydrogen peroxide (e.g. 20 to 50% by weight, preferably 25 to 35% by weight) in alcohols such as methanol or ethanol, ketones such as acetone, or nitriles such as acetonitrile, generally at from 10° to 50° C., preferably 20° to 35° C., in particular 25° to 30° C., and alkyl hydroperoxides, e.g. tert-butyl hydroperoxide, with the addition of a catalyst, e.g. sodium tungstate, pertungstic acid, molybdenum hexacarbonyl or vanadyl acetylacetonate. Some of the said oxidizing agents can be generated in situ.

The compounds V can be prepared by conventional processes for synthesizing aldehydes (cf., for example, Houben-Weyl-Müller, Methoden der Organischen Chemie, Georg Thieme Verlag, Stuttgart 1983, Vol. E 3).

The Examples which follow illustrate the preparation of the active ingredients.

I. PREPARATION OF THE STARTING MATERIALS

EXAMPLE A

Preparation of E/Z-2-(4-fluorophenyl)-3-phenylpropenal 4.2 g of sodium hydroxide in 30 ml of water are added to a solution of 26.5 g of benzaldehyde in 300 ml of methanol. The reaction mixture is cooled to 10° C., and 36 g of 4-fluorophenylacetaldehyde are rapidly added, during which the solution rises to 30°–40° C. The reaction solution is stirred at 40° C. for 10 hours and then cooled and the crystals which have separated out are filtered off with suction. 31.6 g (56%) of E/Z-2-(4-fluorophenyl)-3-phenylpropenal of melting point 87°–94° C. are obtained.

EXAMPLE B

Preparation of cis-2-formyl-2-(4-fluorophenyl)-3-phenyloxirane 67.8 g of E/Z-2-(4-fluorophenyl)-3-phenylpropenal are dissolved in 300 ml of methanol, and 1 ml of concentrated sodium hydroxide solution is added. The reaction solution is stirred at 0° C. while 20.5 g of hydrogen peroxide (about 50% by weight) are slowly added dropwise not allowing the internal temperature to exceed 30° C. After the addition is complete, the mixture is stirred at room temperature for 6 hours, then 100 ml of water are added, and the resulting emulsion is extracted by shaking with methyl tert-butyl ether. The isolated organic phase is then dried over sodium sulfate and concentrated. 55.9 g (77%) of cis-2-formyl-2-(4-fluorophenyl)-3-phenyloxirane are obtained.

II. PREPARATION OF THE FINAL PRODUCTS

EXAMPLE 1

7.4 g of thionyl chloride are added to a solution of 17.5 g of triazole in 75 ml of methylene chloride at 0° C. and under a nitrogen atmosphere. After the addition is complete, the mixture is stirred at room temperature for 30 minutes and then 2 g of methanol and 10 g of cis-2-formyl-2-(4-fluorophenyl)-3-phenyloxirane are added. The reaction mixture is stirred at room temperature for 12–15 hours and then 100 ml of water are added to the solution, and the organic phase is separated off. The remaining aqueous phase is extracted by shaking twice with methylene chloride, and the collected organic phases are washed twice with saturated sodium bicarbonate solution. The isolated organic phase is then dried over sodium sulfate and concentrated, and the residue is purified by flash chromatography on silica gel (9:1 ethyl acetate/n-hexane). 2.3 g (18%) of 1'RS-cis-2-[1-(1,2,4-triazol-1-yl)-1-methoxymethyl]-2-(4-fluorophenyl)-3-phenyloxirane are obtained as a 5:1 diastereomer mixture, melting point 135°–138° C.

The compounds listed in the Table can be prepared as in Example 1.

TABLE

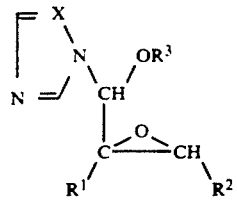

I

| Ex. No. | $R^1$ | $R^2$ | $R^3$ | X | m.p./IR | Isomer |
|---|---|---|---|---|---|---|
| 1 | $4\text{-}F\text{--}C_6H_4$ | $C_6H_5$ | $CH_3$ | N | 135–138° C. | $D_1:D_2 = 5:1$ |
| 2 | $4\text{-}F\text{--}C_6H_4$ | $C_6H_5$ | $CH_3$ | CH | resin | $D_1:D_2 = 4:1$ |
| 3 | $4\text{-}F\text{--}C_6H_4$ | $C_6H_5$ | $C_2H_5$ | N | | |
| 4 | $4\text{-}F\text{--}C_6H_4$ | $2\text{-}Cl\text{--}C_6H_4$ | $CH_3$ | N | | |
| 5 | $4\text{-}F\text{--}C_6H_4$ | $2\text{-}Cl\text{--}C_6H_4$ | $CH_3$ | CH | | |
| 6 | $4\text{-}F\text{--}C_6H_4$ | $2\text{-}Cl\text{--}C_6H_4$ | $C_2H_5$ | N | | |
| 7 | $4\text{-}F\text{--}C_6H_4$ | $2\text{-}Cl\text{--}C_6H_4$ | $C_3H_7$ | N | | |
| 8 | $4\text{-}F\text{--}C_6H_4$ | $2\text{-}Cl\text{--}C_6H_4$ | iso-$C_3H_7$ | N | | |
| 9 | $4\text{-}F\text{--}C_6H_4$ | $2\text{-}Cl\text{--}C_6H_4$ | $C_4H_9$ | N | | |
| 10 | $4\text{-}F\text{--}C_6H_4$ | $3\text{-}Cl\text{--}C_6H_4$ | $CH_3$ | N | | |
| 11 | $4\text{-}F\text{--}C_6H_4$ | $4\text{-}Cl\text{--}C_6H_4$ | $CH_3$ | N | | |
| 12 | $4\text{-}F\text{--}C_6H_4$ | $4\text{-}Cl\text{--}C_6H_4$ | $C_2H_5$ | N | | |
| 13 | $4\text{-}F\text{--}C_6H_4$ | $2,4\text{-}Cl_2\text{--}C_6H_3$ | $CH_3$ | N | | |
| 14 | $4\text{-}F\text{--}C_6H_4$ | $2,4\text{-}Cl_2\text{--}C_6H_3$ | $C_2H_5$ | N | | |
| 15 | $4\text{-}F\text{--}C_6H_4$ | $2\text{-}Cl\text{-}4\text{-}F\text{--}C_6H_3$ | $CH_3$ | N | | |
| 16 | $4\text{-}F\text{--}C_6H_4$ | $2\text{-}CF_3\text{--}C_6H_4$ | $CH_3$ | N | | |
| 17 | $4\text{-}F\text{--}C_6H_4$ | $2\text{-}CF_3\text{--}C_6H_4$ | $CH_3$ | CH | | |

TABLE-continued

I (structure shown: N=CH-N(X)-CH(OR³)-C(R¹)(O)CH(R²), with epoxide between C and CH)

| Ex. No. | R¹ | R² | R³ | X | m.p./IR | Isomer |
|---|---|---|---|---|---|---|
| 18 | 4-F—C₆H₄ | 2-CF₃—C₆H₄ | C₂H₅ | N | | |
| 19 | 4-F—C₆H₄ | 4-CF₃—C₆H₄ | CH₃ | N | | |
| 20 | 4-F—C₆H₄ | 4-CF₃—C₆H₄ | C₂H₅ | N | | |
| 21 | 4-F—C₆H₄ | 2-F—C₆H₄ | CH₃ | N | | |
| 22 | 4-F—C₆H₄ | 2-F—C₆H₄ | C₂H₅ | N | | |
| 23 | 4-F—C₆H₄ | 4-F—C₆H₄ | CH₃ | N | | |
| 24 | 4-F—C₆H₄ | 4-F—C₆H₄ | C₃H₇ | N | | |
| 25 | 4-F—C₆H₄ | 2,4-F₂—C₆H₃ | CH₃ | N | | |
| 26 | 4-F—C₆H₄ | 2,6-F₂—C₆H₃ | CH₃ | N | | |
| 27 | 4-F—C₆H₄ | 2-OCH₃—C₆H₄ | CH₃ | N | | |
| 28 | 4-F—C₆H₄ | 4-tert-butyl-C₆H₄ | CH₃ | N | | |
| 29 | 4-F—C₆H₄ | 4-NO₂—C₆H₄ | CH₃ | N | | |
| 30 | 4-F—C₆H₄ | 4-NH₂—C₆H₄ | CH₃ | N | | |
| 31 | 4-F—C₆H₄ | 2-C₁₀H₇ | CH₃ | N | | |
| 32 | 4-F—C₆H₄ | cyclohexyl | CH₃ | N | | |
| 33 | C₆H₅ | 2-Cl—C₆H₄ | CH₃ | N | | |
| 34 | C₆H₅ | 2-Cl—C₆H₄ | CH₃ | CH | | |
| 35 | C₆H₅ | 2-Cl—C₆H₄ | C₂H₅ | N | | |
| 36 | C₆H₅ | 2-Cl—C₆H₄ | C₃H₇ | N | | |
| 37 | C₆H₅ | 4-Cl—C₆H₄ | CH₃ | N | | |
| 38 | C₆H₅ | 4-Cl—C₆H₄ | CH₃ | CH | | |
| 39 | C₆H₅ | 2,4-Cl₂—C₆H₃ | CH₃ | N | | |
| 40 | C₆H₅ | 2-F—C₆H₄ | CH₃ | N | | |
| 41 | C₆H₅ | 4-F—C₆H₄ | CH₃ | N | | |
| 42 | C₆H₅ | 2-CF₃—C₆H₄ | CH₃ | N | | |
| 43 | C₆H₅ | 2-OCH₃—C₆H₄ | CH₃ | N | | |
| 44 | 2-Cl—C₆H₄ | 2-Cl—C₆H₄ | CH₃ | N | | |
| 45 | 2-Cl—C₆H₄ | 4-Cl—C₆H₄ | CH₃ | N | | |
| 46 | 2-Cl—C₆H₄ | 2-F—C₆H₄ | CH₃ | N | | |
| 47 | 2-Cl—C₆H₄ | 4-F—C₆H₄ | CH₃ | N | | |
| 48 | 4-Cl—C₆H₄ | 2-Cl—C₆H₄ | CH₃ | N | | |
| 49 | 4-Cl—C₆H₄ | 2-Cl—C₆H₄ | CH₃ | CH | | |
| 50 | 4-Cl—C₆H₄ | 4-Cl—C₆H₄ | CH₃ | N | | |
| 51 | 4-Cl—C₆H₄ | 2-F—C₆H₄ | CH₃ | N | | |
| 52 | 4-Cl—C₆H₄ | 4-F—C₆H₄ | CH₃ | N | | |
| 53 | 4-Cl—C₆H₄ | 2-CF₃—C₆H₄ | CH₃ | N | | |
| 54 | 2,4-Cl₂—C₆H₃ | 2-Cl—C₆H₄ | CH₃ | N | | |
| 55 | 2,4-Cl₂—C₆H₃ | 2,4-Cl₂—C₆H₃ | CH₃ | N | | |
| 56 | 4-Br—C₆H₄ | 2-Cl—C₆H₄ | CH₃ | N | | |
| 57 | cyclohexyl | 2-Cl—C₆H₄ | CH₃ | N | | |
| 58 | cyclohexyl | 4-Cl—C₆H₄ | CH₃ | N | | |
| 59 | cyclohexyl | 2-F—C₆H₄ | CH₃ | N | | |
| 60 | cyclohexyl | 4-F—C₆H₄ | CH₃ | N | | |
| 61 | cyclohexyl | 4-Cl—C₆H₄ | C₂H₅ | N | | |
| 62 | cyclohexyl | 4-Cl—C₆H₄ | C₃H₇ | N | | |
| 63 | cyclohexyl | 2,4-Cl₂—C₆H₃ | CH₃ | N | | |
| 64 | cyclohexyl | 2,4-Cl₂—C₆H₃ | CH₃ | CH | | |
| 65 | tetrahydropyran-4-yl | 2-Cl—C₆H₄ | CH₃ | N | | |
| 66 | tetrahydropyran-4-yl | 4-Cl—C₆H₄ | CH₃ | N | | |
| 67 | CH₃ | 2-Cl—C₆H₄ | CH₃ | N | | |
| 68 | CH₃ | 4-F—C₆H₄ | CH₃ | N | | |
| 69 | 4-F—C₆H₄ | 3-pyridyl | CH₃ | N | | |

TABLE-continued

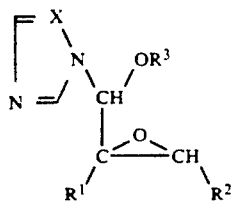

| Ex. No. | R¹ | R² | R³ | X | m.p./IR | Isomer |
| --- | --- | --- | --- | --- | --- | --- |
| 70 | 4-F—C₆H₄ | norbornyl | CH₃ | N | | |
| 71 | 4-F—C₆H₄ | p-C₁₂H₉ | CH₃ | N | | |
| 72 | 4-F—C₆H₄ | 3-cyclohexenyl | CH₃ | N | | |
| 73 | 4-F—C₆H₄ | 2-cyclohexenyl | CH₃ | N | | |

Generally speaking, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia species in cotton and lawns,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in vegetables and fruit.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, for example against *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 2 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 2 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 1 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 2 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 1 is intimately mixed with 97 parts by weight of particulate kaolin. A dust is obtained containing 3% by weight of the active ingredient.

VII. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 1 is intimately mixed with 10 parts by weight of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 2 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

USE EXAMPLES

For comparison purposes, the active ingredient cis-2-(1,2,4-triazol-1-yl-methyl)-2-(tert-butyl)-3-(4-chlorophenyl)-oxirane (A) disclosed in DE-A-3,218,150 was employed.

USE EXAMPLE 1

Action on wheat brown rust

Leaves of pot-grown wheat seedlings of the "Kanzler" variety were dusted with spores of brown rust (*Puccinia recondita*). The posts were then placed for 24 hours at 20° to 22° C. in a high-humidity (90–95%) chamber. During this period the spores germinated and the germ tubes penetrated the leaf tissue. The infected plants were then sprayed to runoff with aqueous liquors containing (dry basis) 80% of active ingredient and 20% of emulsifier. After the sprayed-on layer had dried, the plants were set up in the greenhouse at 20° to 22° C. and a relative humidity of 65 to 70%. The extent of rust fungus spread on the leaves was assessed after 8 days.

The results show that active ingredients nos. 1 and 2, applied as 0.006 wt % spray liquors, had a better fungicidal action (5% attack) than prior art active ingredient A (50% attack).

USE EXAMPLE 2

Action on *Botrytis cinerea* in pimientos

Pimiento seedlings of the "Neusiedler Ideal Elite" variety with 4 to 5 well developed leaves were sprayed to runoff with aqueous suspensions containing (dry basis) 80% of active ingredient and 20% of emulsifier. After the sprayed-on layer had dried, the plants were sprayed with a conidial suspension of the fungus *Botrytis cinerea* and kept in a high-humidity chamber at 22° to 24° C. After 5 days, the disease had spread on the untreated control plants to such an extent that the necroses covered the major portion of the leaves.

The results show that active ingredients nos. 1 and 2, applied as 0.05 wt % spray liquors, had a better fungicidal action (5% attack) than comparative agent A (40% attack).

We claim:

1. A 1-alkoxy-1-azolylmethyloxirane of formula I:

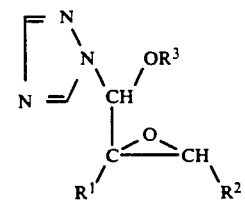

wherein $R^1$ is 4-fluorophenyl; and $R^2$ is $C_3$–$C_8$-cycloalkyl, $C_5$–$C_8$-cycloalkenyl, tetrahydropyranyl, norbornyl, naphthyl, biphenylyl or phenyl, each of which is unsubstituted or mono- to tri-substituted by halogen, nitro, phenoxy, amino, alkyl, alkoxy or haloalkyl of 1 to 4 carbon atoms in each case; and $R^3$ is $C_1$–$C_4$-alkyl, and the acid addition salts and metal complexes thereof which are tolerated by plants.

2. A fungicidal composition containing a solid or a liquid carrier and a fungicidally effective amount of a 1-alkoxy-1-azolylmethyloxirane of the formula I

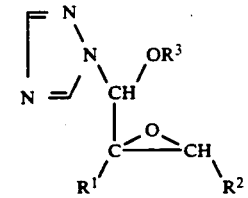

wherein $R^1$ is 4-fluorophenyl; $R^2$ is $C_3$–$C_8$-cycloalkyl, $C_5$–$C_8$-cycloalkenyl, tetrahydropyranyl, norbornyl, naphthyl, biphenylyl or phenyl, each of which is unsubstituted or mono- to tri-substituted by halogen, nitro, phenoxy, amino, alkyl, alkoxy or haloalkyl of 1 to 4 carbon atoms in each case, and $R^3$ is $C_1$–$C_4$-alkyl, or an acid addition salt or metal complex thereof tolerated by plants.

3. A process for combating fungi, comprising: applying a fungicidally effective amount of a 1-alkoxy-1-azolylmethyloxirane of the formula I:

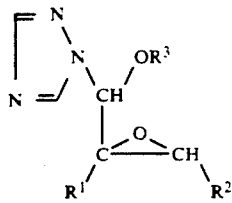

wherein $R^1$ is 4-fluorophenyl; $R^2$ is $C_3$–$C_8$-cycloalkyl, $C_5$–$C_8$-cycloalkenyl, tetrahydropyranyl, norbornyl, naphthyl, biphenylyl or phenyl, each of which is unsubstituted or mono- to tri-substituted by halogen, nitro, phenoxy, amino, alkyl, alkoxy or haloalkyl of 1 to 4 carbon atoms in each case, and $R^3$ is $C_1$–$C_4$-alkyl, or an acid addition salt or metal complex thereof tolerated by plants to areas, plants or seed threatened by fungus attack.

4. A compound as set forth in claim 1, where $R^1$ is 4-fluorophenyl, $R^2$ is phenyl and, $R^3$ is methyl.

5. The composition of claim 2, wherein the composition contains from 0.1 to 95 wt. % of active fungicidal ingredient.

6. The process of claim 3, wherein from 0.02 to 3 kg of fungicidally active ingredient is applied per hectare of area.

* * * * *

UNITED STATES PATENT AND TRADEMARK OFFICE
CERTIFICATE OF CORRECTION

PATENT NO. : 5,128,357
DATED : July 7, 1992
INVENTOR(S) : Rainer Seele et al.

It is certified that error appears in the above-identified patent and that said Letters Patent is hereby corrected as shown below:

On the title page, item [30]:

The Foreign Application Priority Data is incorrect, should be,

--Apr. 6, 1989 [DE] Fed. Rep. of Germany..............3911059--.

Signed and Sealed this

Seventh Day of September, 1993

Attest:

BRUCE LEHMAN

*Attesting Officer*    *Commissioner of Patents and Trademarks*